United States Patent
Bentele et al.

(10) Patent No.: US 8,591,572 B2
(45) Date of Patent: *Nov. 26, 2013

(54) SURGICAL IMPLANT, METHOD FOR THE PRODUCTION AND USE THEREOF

(75) Inventors: Franz Bentele, Nehren (DE); Helmut Goldmann, Tuttlingen (DE)

(73) Assignee: Aesculap AG, Tuttlingen/Donau (DE)

( * ) Notice: Subject to any disclaimer, the term of this patent is extended or adjusted under 35 U.S.C. 154(b) by 878 days.

This patent is subject to a terminal disclaimer.

(21) Appl. No.: 12/385,045

(22) Filed: Mar. 30, 2009

(65) Prior Publication Data

US 2009/0192597 A1 Jul. 30, 2009

Related U.S. Application Data

(63) Continuation of application No. 10/478,128, filed as application No. PCT/EP02/05544 on May 21, 2002, now Pat. No. 7,530,996.

(30) Foreign Application Priority Data

May 21, 2001 (DE) .................................. 101 25 712

(51) Int. Cl.
*A61F 2/06* (2013.01)
*A61F 2/02* (2006.01)
(52) U.S. Cl.
USPC ................. 623/1.51; 623/1.52; 623/23.74
(58) Field of Classification Search
None
See application file for complete search history.

(56) References Cited

U.S. PATENT DOCUMENTS

| 4,530,113 | A | 7/1985 | Matterson | 623/1.51 |
| 5,496,364 | A | 3/1996 | Schmitt | |
| 6,136,022 | A | 10/2000 | Nuñez et al. | |
| 6,547,820 | B1 | 4/2003 | Staudenmeier | 623/1.49 |

FOREIGN PATENT DOCUMENTS

| CH | 684241 A5 | 8/1994 |
| DE | 3830005 C1 | 11/1989 |
| DE | 3830481 A1 | 3/1990 |
| DE | 3913926 A1 | 10/1990 |
| DE | 4128611 A1 | 3/1992 |
| DE | 19912360 A1 | 9/2000 |
| DE | 19912648 A1 | 9/2000 |
| DE | 19954166 A1 | 5/2001 |
| EP | 0 179 600 | 4/1986 |
| EP | 0 327 903 A2 | 8/1989 |
| EP | 0 677 297 A1 | 10/1995 |
| EP | 0 699 423 A2 | 3/1996 |
| GB | 2 247 696 A | 3/1992 |
| WO | WO 92/03107 | 3/1992 |
| WO | WO 97/02789 | 1/1997 |
| WO | WO 98/11198 A1 | 3/1999 |
| WO | WO 99/40875 | 8/1999 |
| WO | WO 00/51524 | 9/2000 |

OTHER PUBLICATIONS

XP000372004: King, M.W. et al., "Designing Polyester Vascular Prostheses for the Future", *Medical Progress through Technology*, Springer-Verlag, vol. 9, No. 4, pp. 217-226, (1983).

*Primary Examiner* — David H Willse
*Assistant Examiner* — Javier Blanco
(74) *Attorney, Agent, or Firm* — Nath, Goldberg & Meyer; Jerald L. Meyer; Scott C. Langford

(57) ABSTRACT

A surgical implant is made from biocompatible fiber material as a woven textile fabric, in particular in the form of a vascular prosthesis, the woven fabric being so configured that its permeability to blood is so low that the blood impregnates the textile fabric upon implantation and seals it off by coagulating, but does not flow through it.

16 Claims, 3 Drawing Sheets

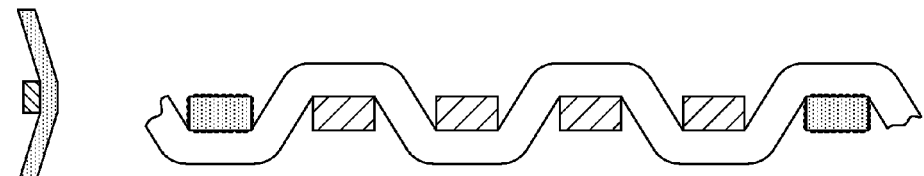
FIG. 4
FIG. 3
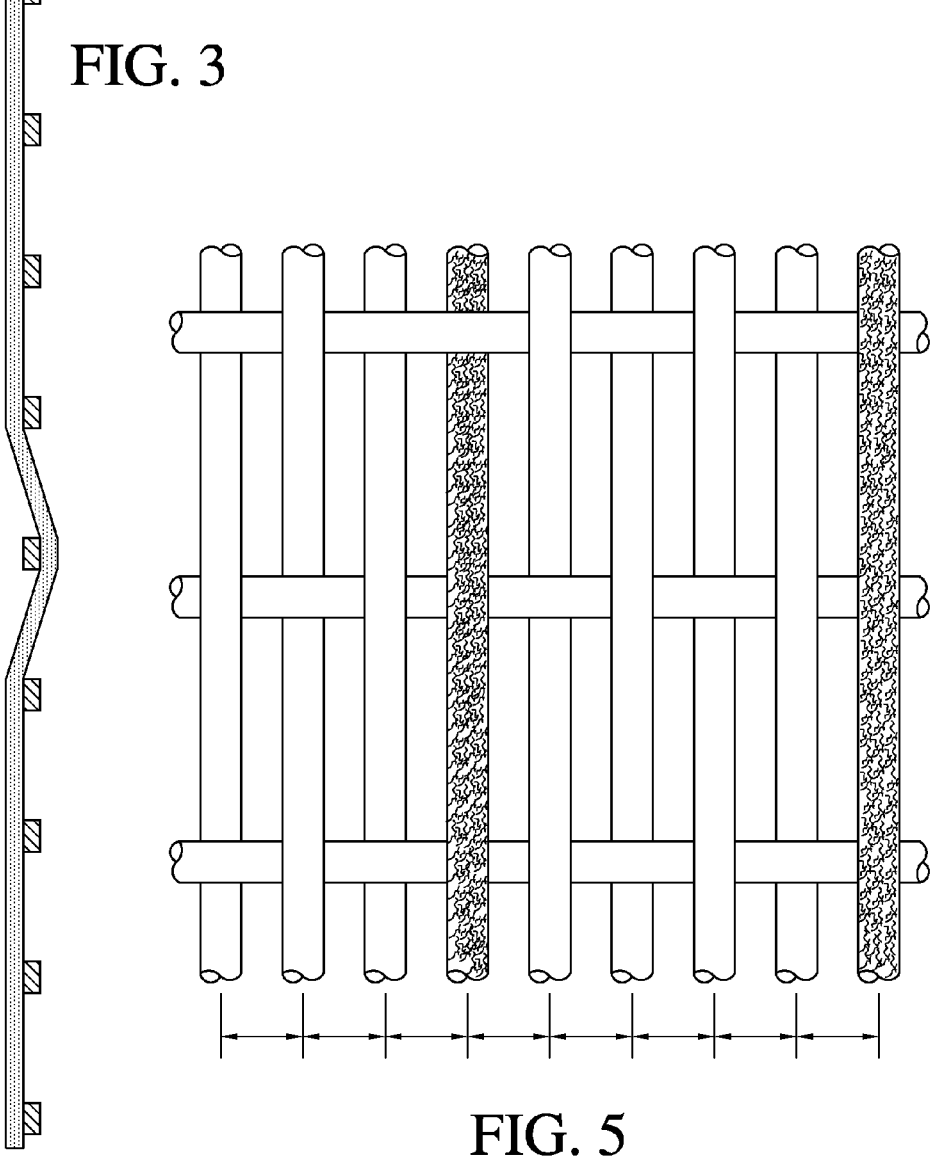
FIG. 5

SURGICAL IMPLANT, METHOD FOR THE PRODUCTION AND USE THEREOF

This is a continuation Application of U.S. Ser. No. 10/478,128, filed Apr. 30, 2004 (now U.S. Pat. No. 7,530,996), which was filed under 35 U.S.C. 371 as a national stage of PCT/EP02/05544, filed 21 May 2002, the entire content of which is hereby incorporated by reference in its entirety.

The invention relates to a surgical implant, a method for its production and its use.

In the medical treatment of humans or animals it is often necessary, in surgical interventions, to support diseased or damaged body parts by means of implants or to replace these body parts partially, or even completely, by means of prostheses. Examples of such implants are vascular prostheses intended to replace damaged parts of blood vessels. Implants are known which have a knitted or woven structure. Moreover, vascular prostheses are known with structured surfaces, for example pleats or velour.

In the known implants, there are problems regarding the process of incorporation because the foreign body constituted by the implant is colonized only slowly by endogenous cells. There are also difficulties involved in sewing the prosthesis in place and connecting it to the patient's body tissue. The porosity of known textile implants can cause leaking, with undesired blood loss. This can lead to increased intraoperative complications, longer interruption of the blood supply to the distal tissues and organs, or bleeding through the vessel walls, with risks of further postoperative complications, impaired incorporation of the implant, or, as a result of this, secondary diseases.

The object is therefore to make available a surgical implant which overcomes the problems of implants from the prior art, becomes incorporated rapidly and without complications in the patient's body, can be produced easily and inexpensively by conventional methods, and is easy to apply in surgical practice.

This object is achieved by means of a surgical implant made from biocompatible fiber material as a woven textile fabric, in particular in the form of a vascular prosthesis, characterized in that the woven fabric is so configured that its permeability to blood, to which anticoagulants have been added, is so low that the blood impregnates the textile fabric upon implantation and seals it off by coagulating.

BRIEF DESCRIPTION OF THE DRAWINGS

FIGS. 2-5 illustrate various exemplary embodiments of the claimed subject matter.

Surprisingly, it was found that an implant according to the present invention becomes incorporated particularly rapidly and without complications. There is no accumulation of blood clots which can permanently interfere with the creation of the neointima or the vessel capsule.

Materials which can be used to form such an implant are biocompatible natural fibers, synthetic fibers, mixed fibers, composite fibers, or mixtures of these. One example of a preferred implant material is polyethylene terephthalate (e.g. available commercially under the brand name Dacron).

The implant according to the invention can have a water permeability in the range of from 100 to 300 ml/cm$^2$·min, in particular of from 150 to 250 ml/cm$^2$·min. These water permeability values were measured at 120 mmHg using the Wesolowski method of determination. In this way the implant is found to be blood-tight after a short time, and the risk of seeping hemorrhage is low.

The implant can advantageously be made so thin that it is possible for blood vessels to grow in. It can also be made so thin that it is possible for nutrients to pass through in order to supply a neointima in the process of formation. Intracellular and capillary diffusion of tissue fluid is possible. During the formation of a neointima, such diffusion from outside is advantageous for nutrient supply. This supply is later provided by means of new vessel infiltrations.

FIGS. 1-5 illustrate various exemplary embodiments of the claimed subject matter. In one exemplary embodiment, the woven fabric can be configured in a thickness of from 0.1 to 0.35 mm, in particular of from 0.15 to 0.25 mm, preferably 0.2 mm. Thickness is determined according to DIN 863.

Figure 1:
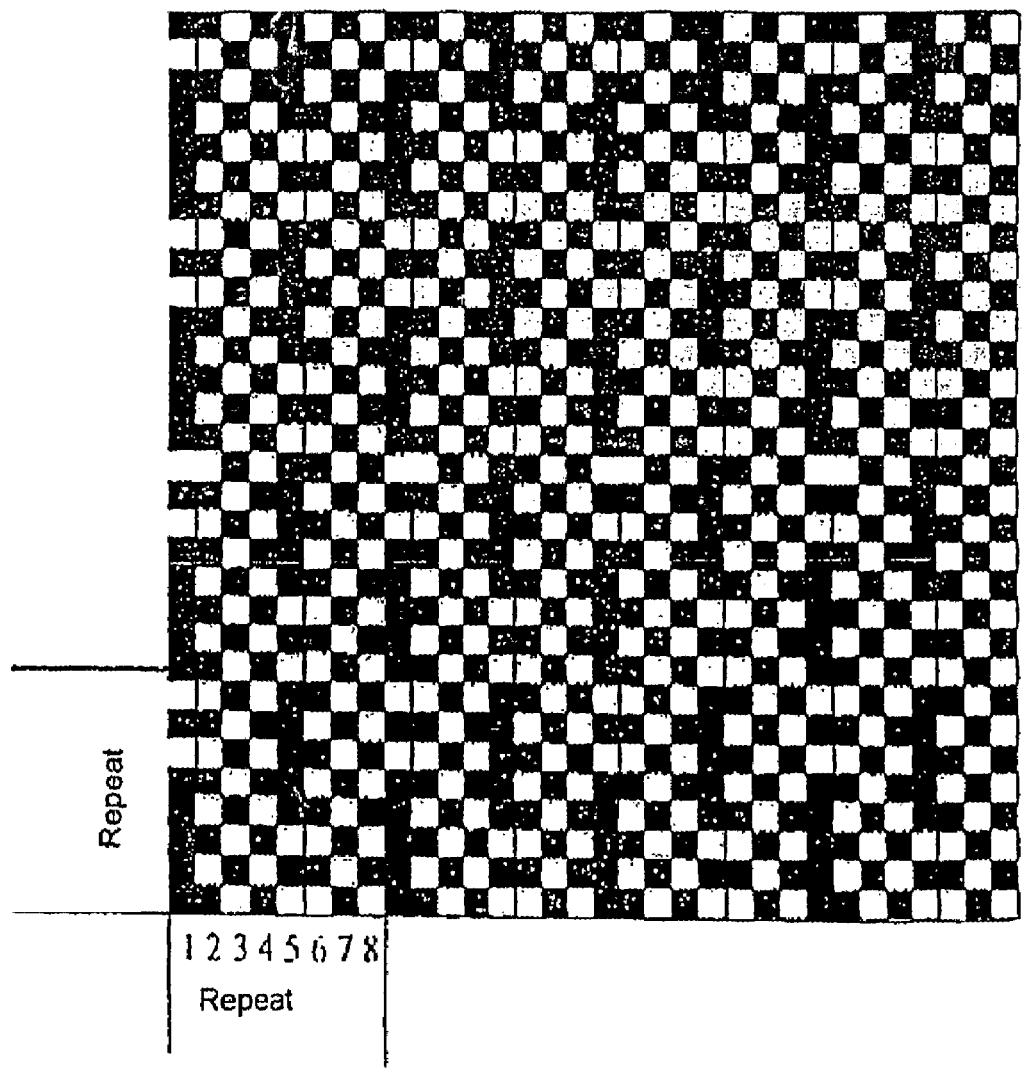
FIG. 1 is a diagram showing a weave pattern of a vascular prosthesis fabricated as a basic woven fabric in a plain weave, with floating in the warp direction.
Figures 2, 5:
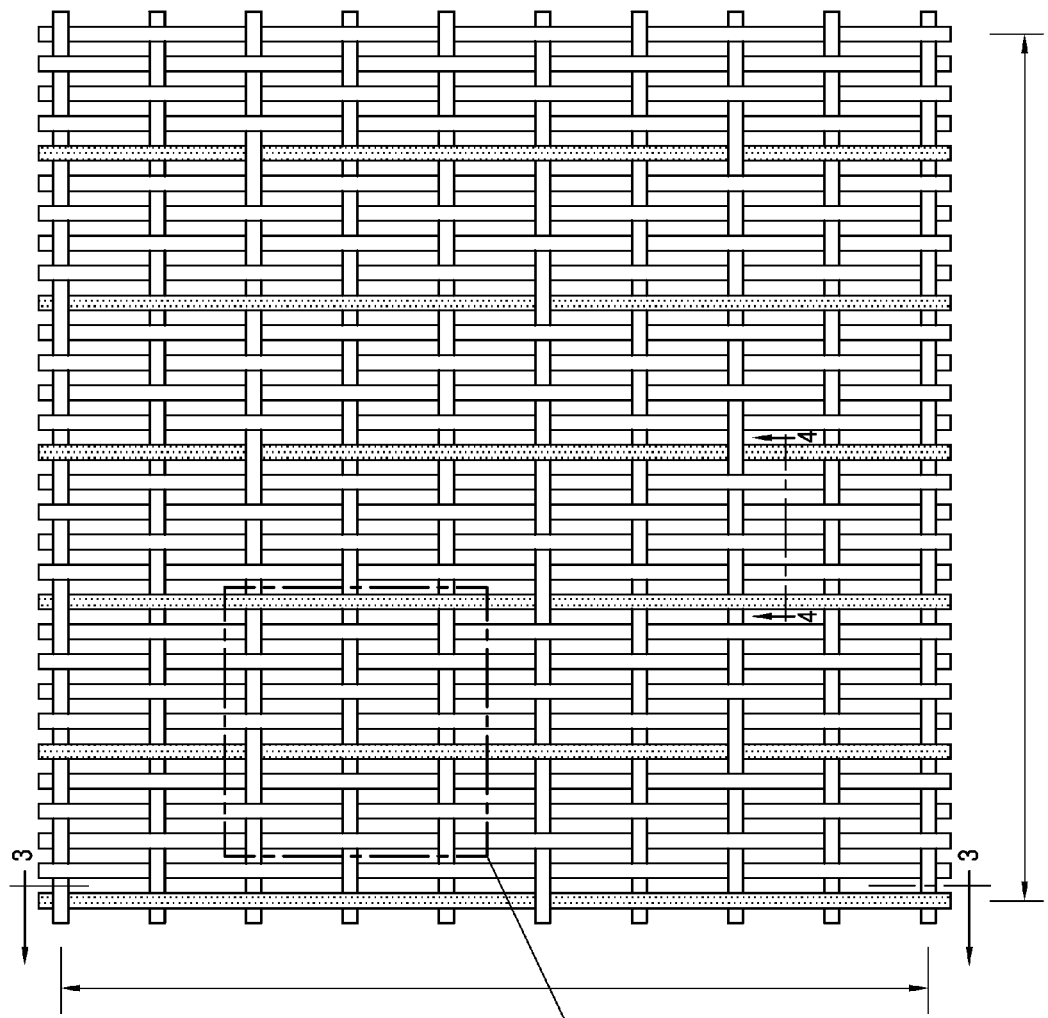

In a particular embodiment, the woven fabric of the implant can be configured with threads lying flat alongside one another without close contact (as shown in FIGS. 2-5, for example). The woven fabric can be preferably configured with threads of yarn size 10 to 200 dtex, 10 to 200 filaments per thread, and a twisting of the yarn of 50 to 500 turns/m. In addition, the woven fabric can be configured with 30 to 120 warp threads and 10 to 70 weft threads per centimeter (a not-to scale exemplary version of which is shown in FIG. 2), in other examples, 40 to 80 warp threads and 20 to 50 weft threads. According to the exemplary embodiment shown in FIG. 1, the woven fabric can preferably be configured with a repeat of 8×8.

In the woven fabric of the implant, the spacing of the threads with respect to one another can correspond to the thread width, so that the threads lie close alongside one another. The small spacing between individual fibers is important for irritation-free and rapid incorporation of the implant. If very large cells are able to collect between implant fibers, the ingrowth of the desired neointima is obstructed. The individual fibers of the thread can also lie flat alongside one another in the woven fabric, so that the thread cross section is not round but instead oval. Typically, about 20 individual fibers can lie alongside one another in a flat thread in the woven fabric. Flat fiber bundles with substantially parallel fibers can lie in particular on the surface of the implant fabric.

In a preferred embodiment, the woven fabric of the implant can be configured essentially in a plain weave, in particular having a base structure with a plain weave.

In a particular embodiment, it is possible for only flat threads to be used as warp threads. In one possible embodiment, it is possible for only textured threads to be used as warp threads. Advantageously, the woven fabric can be made up of a combination of flat and textured threads. The overall ratio of flat threads to textured threads can preferably be between 1:1 and 6:1, in particular 3:1. In a particular embodiment, the woven fabric can according to the invention contain at least 50% flat threads, that is to say nontextured threads.

In a preferred embodiment, flat and textured threads, particularly in alternating sequence, can be used as warp threads, the ratio of flat threads to textured threads being between 2:1 and 1:2, in particular 1:1.

In a particularly preferred embodiment of the implant according to the invention, it is possible for only flat threads to be used as weft threads. In another embodiment, flat and textured threads, particularly in alternating sequence, can be used as weft threads, the ratio of flat threads to textured threads being between 5:1 and 1:5. The implant may advantageously be characterized by flat threads being lightly plied.

In an exemplary embodiment of the implant (as shown, for example, in FIGS. 2-5), floating threads can be included, in particular floating threads extending in the warp direction. Such a floating thread is present additionally to and parallel to a warp thread in the plain weave. At the site where it lies in plain weave, the additional floating thread runs together with the parallel warp thread and joins up again with the warp thread after the floating. The floating threads can lie flat in the woven fabric surface and do not form loops. Optionally, one or more of the floating threads can be textured. In an exemplary embodiment, a floating textured thread in the weave can lie in proximity to two flat threads running in the same direction of the woven fabric. A float in the warp direction may have a favorable effect on the incorporation behavior in the case of a tubular implant.

In a particular embodiment, a woven fabric can be made up only of flat threads with a float of textured threads. In another embodiment, a woven fabric can be made up of alternating flat and textured threads with a float of textured threads, in which case in particular only every second textured thread has a float.

It is particularly advantageous that the floating threads can preferably extend only in the warp direction. In another embodiment, the floating threads can extend both in the warp direction and in the weft direction, and in particular the floating threads can be included in the warp direction and in the weft direction in different numbers.

According to an exemplary embodiment (as shown in FIGS. 2-5 for example), the float can preferably extend over more than 2 threads, in particular over 3 to 10 threads, preferably over 4 to 6 threads. The float can advantageously be 4 to 6 over 1, preferably 5 over 1. In a preferred embodiment, with a repeat of 8.times.8, a float over 5 under 1 over 1 under 1 can be included. In the float, an uneven number is preferred, since otherwise the floating thread no longer lies parallel to an adjacent woven fabric thread of the plain weave.

According to an exemplary embodiment (as shown in FIG. 1 for example), the ratio of floating threads to warp threads can be between 1:20 to 1:1, in particular between 1:10 to 1:2, preferably 1:3. In other words, floating threads can be present in a proportion of about 5 to 50%, in particular of 9 to 33%, preferably 25%, in relation to warp threads in the woven fabric. The floats of adjacent floating threads can preferably be offset in the warp direction, with preferably at least some of the floats overlapping.

In certain exemplary embodiments, the mutual spacing between floating threads in the weft direction can in each case be identical. A not-to-scale version of this is shown in FIG. 5 for example, with the arrows indicating that the distances in the weft direction are identical. In certain exemplary embodiments, at least three threads of the basic woven fabric can lie between these. A maximum of two overlaps of warp threads can lie alongside one another in the weft direction.

In certain exemplary embodiments, the implant can be characterized in that the floating threads float only on one surface of the implant, which is preferably the outer surface in the case of a vascular prosthesis. In a refinement of this, a float can have only a slight pile height (shown in FIG. 4 for example), which can be achieved by the texturing of the threads (shown in FIG. 5, for example).

The woven fabric can advantageously be shrunk by thermal treatment. In particular, textured threads in the woven fabric can be opened by the shrinkage. In addition, the pile height of the woven fabric of the implant can be influenced by shrinkage.

According to the invention, the implant, particularly on at least one side of the woven fabric, can have a structure favoring ingrowth of a neointima. This is preferably a substantially pure plain weave with mainly flat threads and a small proportion of open textured threads. Mesothelial cells are able, starting from vessel stumps, to form a new thin and smooth neointima.

In a refinement of this as shown in FIGS. 2-5 for example, the implant can have, at least on one side, preferably the other side of the woven fabric, a structure favoring the formation of a thin fibrous capsule. Compared to the other side, this side has the floats consisting in particular of textured threads. Fibroblasts grow in from surrounding tissue and form the collagen for external encapsulation free from blood clots.

According to the invention, the woven fabric can be configured as a simple velour. Advantageously, a velour structure of the implant may be provided only on the vessel's outside. Moreover, the inner side of the vessel can have a structure favoring ingrowth of a neointima. Such a layer of mesothelial cells can form in particular on a smooth wall of the woven fabric structure. Preferably, the implant according to the invention can have on one side, in particular on the side lying to the inside in the case of a vascular prosthesis, textured surface threads at less than 30%, in particular at less than 20% of the intersections of warp and weft. By parallel arrangement of textured additional floating threads with flat threads of the basic woven fabric running in the same direction, the proportion of textured threads is further reduced by partial overlapping of the textured thread by the flat thread. Moreover, preferably on the outward side in the case of a vascular prosthesis, the implant according to the invention can, at fewer than half and in particular at fewer than a third of the intersections of warp and weft, have textured threads lying on the surface. In this way, on one side of the implant fabric with preferably only a plain weave, the floating thread can be at least partially covered by normal, flat, parallel threads of the basic fabric of the plain weave, and, on the other side, can extend on a normal thread of the basic fabric of the plain weave and lie substantially exposed on the fabric surface.

By the preferable use of the plain weave on the inner side of a vascular prosthesis, a smooth inner surface is produced. On the outside, by contrast, the textile structure according to the invention, with more use of textured yarns, produces a voluminous structure compared to the inner side. By means of this more strongly structured outer surface, a density gradient (porosity gradient) is obtained toward the inner surface of the vascular prosthesis, resulting in improved ingrowth of the blood vessels and, at the same time, more favorable formation of the neointima.

If desired in special cases, a rapidly absorbable coating, for example of gelatin or other suitable natural or synthetic materials, can be applied to the implant according to the invention. However, this is not generally necessary, because the woven fabric seals upon the first passage of blood.

The invention also relates to a method for the production of a surgical implant from biocompatible fiber material as a woven textile fabric, in particular in the form of a vascular prosthesis, said method being characterized in that, by means of weaving, a structure is formed whose permeability to blood, to which anticoagulants have been added, is so low that the blood impregnates the textile fabric and seals it off by coagulating.

From a textile fabric produced according to the invention, an implant of desired shape can be produced by textile techniques known to those skilled in the art. For use as a vascular prosthesis, the implant can be configured in the shape of a tube with a suitable lumen.

Moreover, one or more medically active substances can advantageously be added to the implant according to the invention. These active substances may be, for example, medicaments, antibiotics, antiseptics, clotting factors, growth factors and the like.

The implant produced according to the invention can be made ready for medical use in a manner known per se. In particular, the material according to the invention can be suitably sterilized. An appropriate sterilization method can be chosen from the usual physical or chemical methods for inactivation of microorganisms or can be a combination of such methods. One possible sterilization method involves treatment with gamma radiation. Another method of sterilizing the implant material according to the invention for medical purposes involves using ethylene oxide. The medical implant produced can advantageously be cut to the appropriate size and suitably packed ready for use.

The invention further relates to the use of a surgical implant, in particular in the form of a vascular prosthesis for treating blood vessel defects in human medicine and veterinary medicine.

When the vascular prosthesis produced according to the invention was tested on animals (dogs), it was found to be blood-tight. To implant the vascular prosthesis according to the invention as an infrarenal aorta replacement, the affected portion of the aorta is exposed, the proximal and distal ends of the vessel are clamped, and the anticoagulant heparin is injected. After resection of the exposed portion, the proximal anastomosis is established. The distal end of the prosthesis is then likewise closed with a clamp, and the proximal clamp is briefly opened so that heparinized blood passes into the implant and displaces the air contained therein. The proximal clamp is then closed for 15 seconds, and the blood emerging through the implant is swabbed up. Renewed opening of the clamped proximal end of the prosthetic implant causes a second pressure surge of blood, already with considerably less blood flowing through the prosthesis. The blood penetrating into the woven fabric of the implant coagulates in the vessel wall and thus leads to sealing of the vascular prosthesis. Blood has to run through about two to three times before the vascular prosthesis is sealed off. The distal end of the implant is then also closed by suturing.

After implantation, a thin layer of fibrin quickly forms in the wall of the vascular prosthesis. This is physiologically broken down without problem, while a neointima and an outer layer of collagen are built up. Surprisingly, after just three months, there has been uniform formation of a bright neointima. Three months after implantation there is also a thin transparent fibrous capsule. After six months, the implant has become incorporated without complications and without inflammation.

In the implant according to the invention, it is not just the porosity that is important, but also the size of the pores and the pore size distribution, produced by the different density of the thread arrangement with different air content in the woven wall. Only minimal bleeding occurs in the wall, and so there is little in the way of blood clots, the presence of which may cause problems and which have to be broken up.

Further features and details of the invention will become clear from the following description of a preferred embodiment which is given as an example and with reference to the accompanying figure. The individual features can be implemented singly, or can be implemented several in combination with one another. The example serves only to illustrate the present invention, and the latter is in no way intended to be restricted thereto.

EXAMPLE

A vascular prosthesis is made from biocompatible synthetic fiber material (polyethylene terephthalate) by weaving of a basic woven fabric in a plain weave, with floating in the warp direction. The weave pattern is shown in FIG. 1.

The warp threads used are flat (100 filaments 80 dtex Z-twist 240 turns) and textured (100 filaments 80 dtex Z-twist 140 turns) threads, every third warp thread of the fabric of the plain weave being textured. The weft comprises only flat threads (100 filaments 80 dtex). The floating thread is textured (50 filaments 40/2 dtex).

All warp and weft threads are arranged in a plain weave. The woven fabric is configured with 31 weft threads and 68 warp threads per centimeter. In a repeat of 8×8, the floating thread is included additionally to the 1st and 5th warp thread. The floating is offset over three warp threads. In the weft direction, the floating thread in each case floats over five weft threads, so that the float appears only on one side of the woven fabric.

In this way, four textured threads are present in the warp direction per repeat, two of them in the basic fabric of the plain weave and two of them as additional floating threads. The additional textured floating threads each lie between two flat threads. Since the floating thread is textured; it forms a structure on one surface of the woven fabric. On the other side of the woven fabric, the floating thread lies alongside the warp thread in the plain weave and on this side does not contribute to a structuring.

The water permeability of this woven fabric lies in the range of 200+50 ml/cm$^2$/min, as measured at 120 mmHg by the Wesolowski method of determination.

The wall thickness of the uncoated prosthesis is 0.15 to 0.25 mm. The wall thickness is measured in accordance with DIN 863 by means of a micrometer gage whose measurement spindle is driven via a coupling. The force acting on the measurement surface is 5 to 10 N. The measurement is performed on a vascular prosthesis cut open, with any creasing being smoothed out.

For vascular prostheses with an external diameter of from 6 mm to 38 mm, the wall thickness of the woven fabric is approximately the same, with a deviation of +0.01 mm.

The invention claimed is:

1. A surgical implant made from biocompatible fiber material as a woven textile fabric, in the form of a vascular prosthesis, having an inner surface and an outer surface, the inner surface is substantially smooth, and the outer surface is structured, wherein;
    the woven fabric is configured in a plain weave, including a base structure with a plain weave, and wherein the woven fabric has a water permeability in the range of from 100 to 300 ml/cm$^2$·min so configured that its permeability to blood, to which anticoagulants have been added, is so low that the blood impregnates the textile fabric upon implantation and seals it off by coagulating;
    only flat threads are used as warp threads;
    only flat threads are used as weft threads; and
    floating threads are included; wherein the floating threads extend only in the warp direction, and the weft direction is devoid of any floating threads,
    wherein the floating threads lie flat in the woven fabric surface and do not form loops, and
    wherein one or more of the floating threads are textured.

2. The implant as claimed in claim 1, wherein the woven fabric is so thin that it is possible for blood vessels to grow through.

3. The implant as claimed in claim 1, wherein the woven fabric is so thin that it is possible for tissue fluid to pass through in order to supply a neointima in the process of formation.

4. The implant as claimed in claim 1, wherein the woven fabric is configured in a thickness of from 0.1 to 0.35 mm.

5. The implant as claimed in claim 1, wherein the woven fabric is configured with threads lying flat alongside one another without close contact.

6. The implant as claimed in claim 1, wherein the woven fabric is configured with threads of yarn size 10 to 200 dtex, 10 to 200 filaments per thread, and a twisting of the yarn of 50 to 500.

7. The implant as claimed in claim 1, wherein the woven fabric is configured with 30 to 120 warp threads and 10 to 70 weft threads per centimeter.

8. The implant as claimed in claim 1, wherein, in the weave, a floating textured thread lies in proximity to two flat threads running in the same direction of the woven fabric.

9. The implant as claimed in claim 1, wherein the floating extends over more than 2 threads.

10. The implant as claimed in claim 1, wherein the floating is 4 to 6 over 1 thread, a plain weave being preferably provided in each case between two floats.

11. The implant as claimed in claim 1, wherein the ratio of floating warp threads to warp threads lying in the plain weave is between 1:20 to 1:3.

12. The implant as claimed in claim 1, wherein the mutual spacing between floating threads in the weft direction is in each case identical.

13. The implant as claimed in claim 1, wherein the floating threads are only on one surface of the implant.

14. The implant as claimed in claim 1, wherein a float has only a small pile height, occasioned by the texturing of the threads.

15. The use of the implant as claimed in claim 1 in surgery in human medicine and veterinary medicine.

16. A method for the production of an implant for use in surgery and made from biocompatible fiber material as a woven textile fabric in the form of a vascular prosthesis, the implant having an inner surface and an outer surface, the inner surface is substantially smooth, and the outer surface is structured, the method comprising the steps of:

weaving a structure such that;

the woven fabric is configured in a plain weave, including a base structure with a plain weave, and wherein the woven fabric has a water permeability in the range of from 100 to 300 ml/cm$^2$·min so configured that its permeability to blood, to which anticoagulants have been added, is so low that the blood impregnates the textile fabric upon implantation and seals it off by coagulating;

only flat threads are used as warp threads;

only flat threads are used as weft threads; and floating threads are included; wherein the floating threads extend only in the warp direction, and the weft direction is devoid of any floating threads, wherein the floating threads lie flat in the woven fabric surface and do not form loops, and wherein one or more of the floating threads are textured.

\* \* \* \* \*